US009129047B2

(12) United States Patent
Minaie et al.

(10) Patent No.: US 9,129,047 B2
(45) Date of Patent: Sep. 8, 2015

(54) PROGRAMMING AND BOLUS MONITORING DEVICE FOR AN IMPLANTABLE DRUG PUMP

(75) Inventors: Pedrum Minaie, Stevenson Ranch, CA (US); Daniel Hernandez Villegas, Grenada Hills, CA (US); Brian Michael Shelton, Northridge, CA (US)

(73) Assignee: MEDALLION THERAPEUTICS, INC., Santa Clarita, CA (US)

( * ) Notice: Subject to any disclaimer, the term of this patent is extended or adjusted under 35 U.S.C. 154(b) by 1946 days.

(21) Appl. No.: 11/866,938

(22) Filed: Oct. 3, 2007

(65) Prior Publication Data

US 2009/0093756 A1 Apr. 9, 2009

(51) Int. Cl.
*G06F 19/00* (2011.01)
*A61M 5/142* (2006.01)
*A61M 5/172* (2006.01)
*A61M 5/14* (2006.01)

(52) U.S. Cl.
CPC ....... *G06F 19/3406* (2013.01); *A61M 5/14276* (2013.01); *A61M 5/172* (2013.01); *G06F 19/3468* (2013.01); *A61M 2005/1405* (2013.01); *A61M 2205/3523* (2013.01)

(58) Field of Classification Search
CPC ............ A61M 5/14276; A61M 5/172; A61M 2205/3523; A61M 2205/3507; A61M 2005/1405; G06F 19/3468; G06F 19/3406
USPC ............ 604/65–67, 131, 151, 246, 502–505, 604/512, 890.1, 891.1
See application file for complete search history.

(56) References Cited

U.S. PATENT DOCUMENTS

| 4,390,022 | A | 6/1983 | Calfee et al. |
| 4,404,972 | A | 9/1983 | Gordon et al. |
| 5,342,408 | A | 8/1994 | deCoriolis et al. |
| 5,350,407 | A | 9/1994 | McClure et al. |
| 6,206,850 | B1 * | 3/2001 | O'Neil .............................. 604/80 |
| 6,923,784 | B2 | 8/2005 | Stein |
| 7,024,245 | B2 | 4/2006 | Lebel et al. |
| 8,352,041 | B2 * | 1/2013 | Das et al. ........................ 607/60 |
| 2002/0038137 | A1 | 3/2002 | Stein |
| 2004/0210267 | A1 * | 10/2004 | Lebel et al. ..................... 607/32 |
| 2005/0027254 | A1 * | 2/2005 | Vasko ........................... 604/131 |
| 2005/0177096 | A1 | 8/2005 | Bollish et al. |
| 2006/0041223 | A1 * | 2/2006 | Dewing et al. ............. 604/93.01 |
| 2006/0212080 | A1 | 9/2006 | Hartley et al. |
| 2006/0212084 | A1 | 9/2006 | Yost et al. |

* cited by examiner

*Primary Examiner* — Theodore Stigell
*Assistant Examiner* — Benjamin Koo
(74) *Attorney, Agent, or Firm* — Henricks, Slavin & Holmes LLP

(57) ABSTRACT

A programming device for an implantable drug pump includes a display device, a communication device, and a controller. The communication device is adapted to facilitate a communication link between the programming device and an implantable drug pump. The controller adapted to receive bolus data stored on the implantable drug pump when the communications link has been established, to process the bolus data, and to control the display device to generate a visual representation of numbers of bolus attempts for multiple periodic time intervals.

9 Claims, 7 Drawing Sheets

PROGRAMMING AND BOLUS MONITORING DEVICE FOR AN IMPLANTABLE DRUG PUMP

BACKGROUND OF THE INVENTION

1. Field of Invention

The present invention relates generally to implantable medical devices and, in particular, to an implantable drug pump programming device that provides bolus monitoring functionality.

2. Description of the Related Art

In addition with providing therapy at different rates during the day, intrathecal drug delivery pump devices allow patients to request additional drug to be delivered during times when extra relief is needed. When a patient visits the clinic, the clinician typically can only rely on anecdotal data to determine whether the patient's patient-controlled analgesia (PCA) regime is providing adequate relief.

It would be helpful to be able to provide a clinician with a way to see a visual representation of actual bolus data to be able to more rapidly ascertain whether the PCA regime in conjunction with the daily delivery regime is providing adequate relief. It would also be helpful to be able to provide a visual indication of when boluses were requested that allows the clinician to determine if further action needs to be taken. It would also be helpful to be able to provide a programming device (for an implantable drug pump) that addresses the foregoing considerations.

SUMMARY OF THE INVENTION

In an example embodiment, a programming device for an implantable drug pump includes a display device, a communication device adapted to facilitate a communication link between the programming device and an implantable drug pump, and a controller adapted to receive bolus data stored on the implantable drug pump when the communications link has been established, to process the bolus data, and to control the display device to generate a visual representation of numbers of bolus attempts for multiple periodic time intervals.

In an example embodiment, a programming device for an implantable drug pump includes a display device, a communication device adapted to facilitate a communication link between the programming device and an implantable drug pump, and a controller adapted to receive bolus data stored on the implantable drug pump when the communications link has been established, to process the bolus data, and to control the display device to generate a visual representation of a daily drug delivery profile (e.g., determined from the implantable drug pump) and an average patient-controlled analgesia (PCA) dose profile determined from the bolus data.

The above described and many other features of the present invention will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

DETAILED DESCRIPTION OF THE EXEMPLARY EMBODIMENTS

The following is a detailed description of the best presently known modes of carrying out the invention. This description is not to be taken in a limiting sense, but is made merely for the purpose of illustrating the general principles of the invention.

The present remote controls or programmers have application in a wide variety of medical device systems. One example of such a system is an implantable infusion device system and the present invention is discussed in the context of implantable infusion device systems. The present invention is not, however, limited to implantable infusion device systems and is instead also applicable to other medical device systems that currently exist, or are yet to be developed. For example, the present invention is applicable to other ambulatory medical device systems. Such systems include, but are not limited to, externally carried infusion pump systems, implantable pacemaker and/or defibrillator systems, implantable neural stimulator systems, and implantable and/or externally carried physiologic sensor systems.

Figure 1:
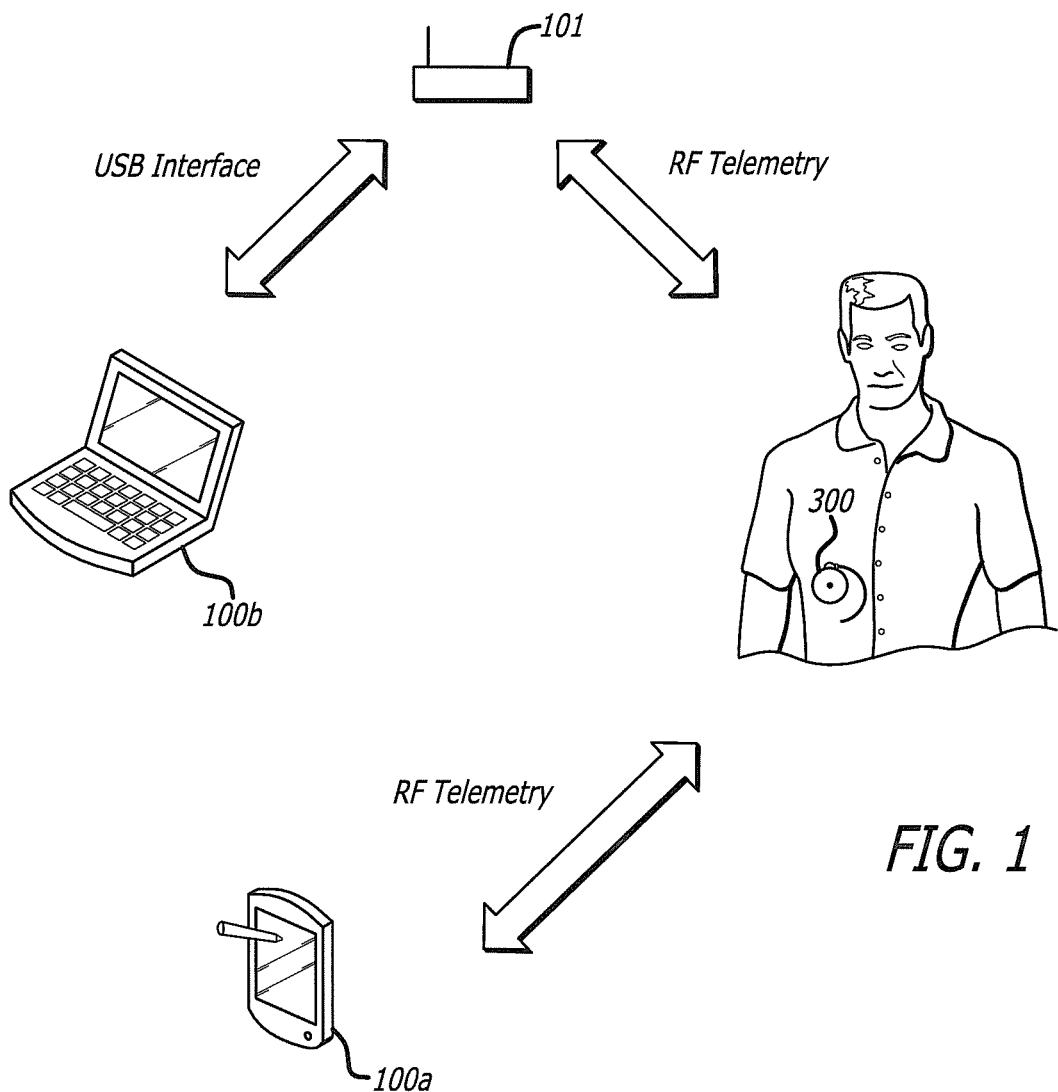
FIG. 1 illustrates an implantable medical device and example programmers/controllers, which embody the implantable drug pump programming devices described herein.

One example of a programmer in accordance with the present invention is an implantable infusion device system. The implantable infusion device system may include any one of the remote controls or programmers described herein in combination with an implantable infusion device. FIG. 1 illustrates an implantable medical device 300 and example programmers/controllers, which embody the drug delivery safety systems described herein. The example programmers/controllers include a programmer 100a (such as a portable computing device (PCD) or personal digital assistant (PDA)) and a clinician programmer 100b (such as a clinician programmer/field support system). In this example, the programmer 100a includes a communication device which facilitates radio frequency (RF) communications with the implantable medical device 300 so that RF telemetry can be communicated between the devices. Also in this example, the clinician programmer 100b is connected to a programmer interface module 101 with a USB Interface; the programmer interface module 101, in turn, facilitates RF communications between the clinician programmer 100b and the implantable medical device 300. It should be understood that other types of programmers/controllers as well as other communications interfaces can also be employed.

Figure 2:
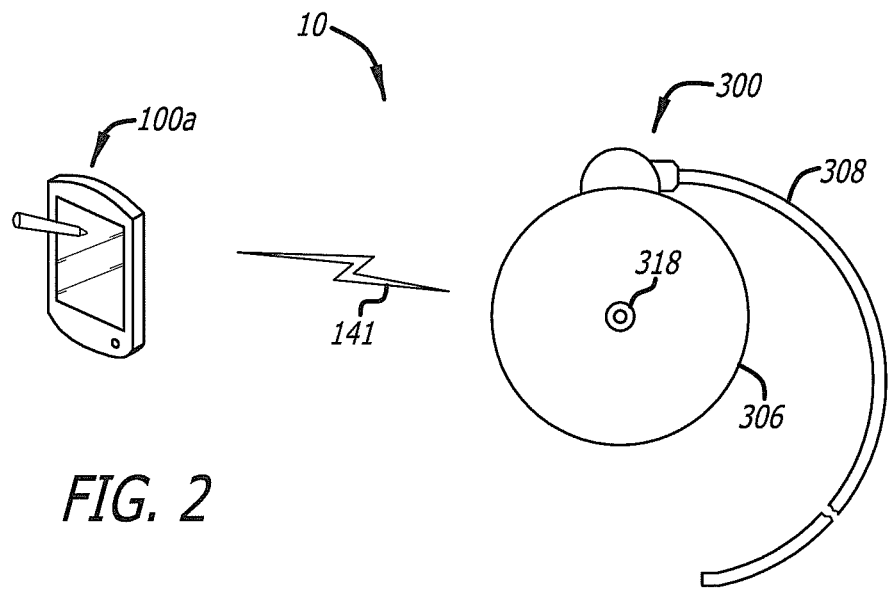
FIG. 2 is a plan view of a programming device in accordance with one embodiment of the present invention, shown establishing a communications link with an implantable medical device.

Referring to FIG. 2, in an example embodiment, an implantable medical device system 10 includes a programmer 100a and an implantable medical device 300. In an example embodiment, the programmer 100a includes a battery or other power source 136, a controller 138, such as a microprocessor, microcontroller or other control circuitry, memory 139, a user input mechanism 142 (such as a keyboard, mouse, touch screen and/or voice recognition device), one or more LEDs 146 (and/or alarm 147), and a display 148. The memory 139 can also be contained within the controller 138 (e.g., within a microcontroller). By way of example and not of limitation, the alarm 147 can include one or more of an audio speaker and a vibration device. A communication device 140 (including an antenna if necessary) is also provided. In an example embodiment, the display 148 is a touch screen configured to receive user inputs, i.e., at least a portion of the functionality of the user input mechanism 142 is provided by the display 148.

The communication device 140 establishes a communications link 141 (e.g., an RF communications link) with the implantable medical device 300. Although the present invention is not limited to any particular communication device, in an example embodiment, the communication device 140 is a telemetry device that transmits an RF signal at a specified frequency or set of frequencies. In an example implementation, there are five channels. The RF signal may, in some instances, be a carrier signal that carries bit streams. The communication device 140 is also configured to receive signals from the implantable medical device 300. Other exemplary communication devices include oscillating magnetic field communication devices, static magnetic field communication devices, optical communication devices, ultrasound communication devices and direct electrical communication devices.

In this example embodiment, the implantable medical device 300 is an implantable infusion device and includes a medication reservoir 302 and a pump or other fluid transfer device 304 within a housing 306. The pump 304 transfers medication from the reservoir 302 through a catheter 308 to the target region within the body. Operation of the implantable medical device 300 is controlled by a controller 310, such as a microprocessor, microcontroller or other control circuitry, in accordance with instructions stored in memory 312. Power is provided by a battery or other power source 314. An alarm 316 (e.g., an audible alarm such as an audio speaker, and/or a vibration device) may also be provided in order to inform the patient, for example, when the amount of medication in the reservoir 302 is low or when the amount of energy stored in the battery 314 is low. A refill port 318, which allows the reservoir to be refilled while the implantable medical device 300 is within the patient, is positioned on the exterior of the housing 306.

A communication device 320 is also provided. In this example embodiment, the communication device 320 is configured to receive signals from, and transmit signals to, the programmer 100a. In an example embodiment, the communication device 320 is a telemetry device that transmits and receives RF signals at a specified frequency or set of frequencies. The RF (or other) signal may, in some instances, be a carrier signal that carries bit streams.

It should be noted here that, in the context of the present invention, different types and/or combinations of user input devices can be employed with any given programmer/controller device. As illustrated for example in FIG. 4, the exemplary programmer 100c includes a housing 102c and a touch screen 228. A controller and a communication device (not shown) are also provided. The touch screen 228 may be used to display one or more button configurations in order to allow the user to accomplish various tasks. At least one of the displayed buttons is a bolus delivery button 104c. The housing 102c may also be provided with one or more button control elements 106c (e.g. buttons), which are operably connected to the controller, and a power on/off button 230.

Figures 4, 5:
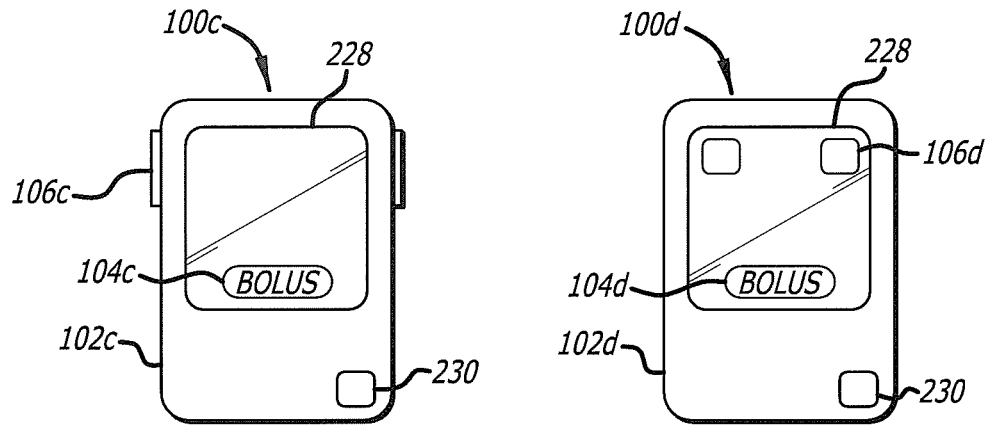
FIG. 4 is a plan view of a programming device in accordance with another embodiment of the present invention.
FIG. 5 is a plan view of a programming device in accordance with still another embodiment of the present invention.

One or more button control elements may, alternatively, be provided on a touch screen. Turning to FIG. 5, the exemplary programmer 100d includes a housing 102d, a touch screen 228 that may be used to, among other things, display a bolus delivery button 104d and a pair of button control elements 106d, and a power on/off button 230.

Figure 3:
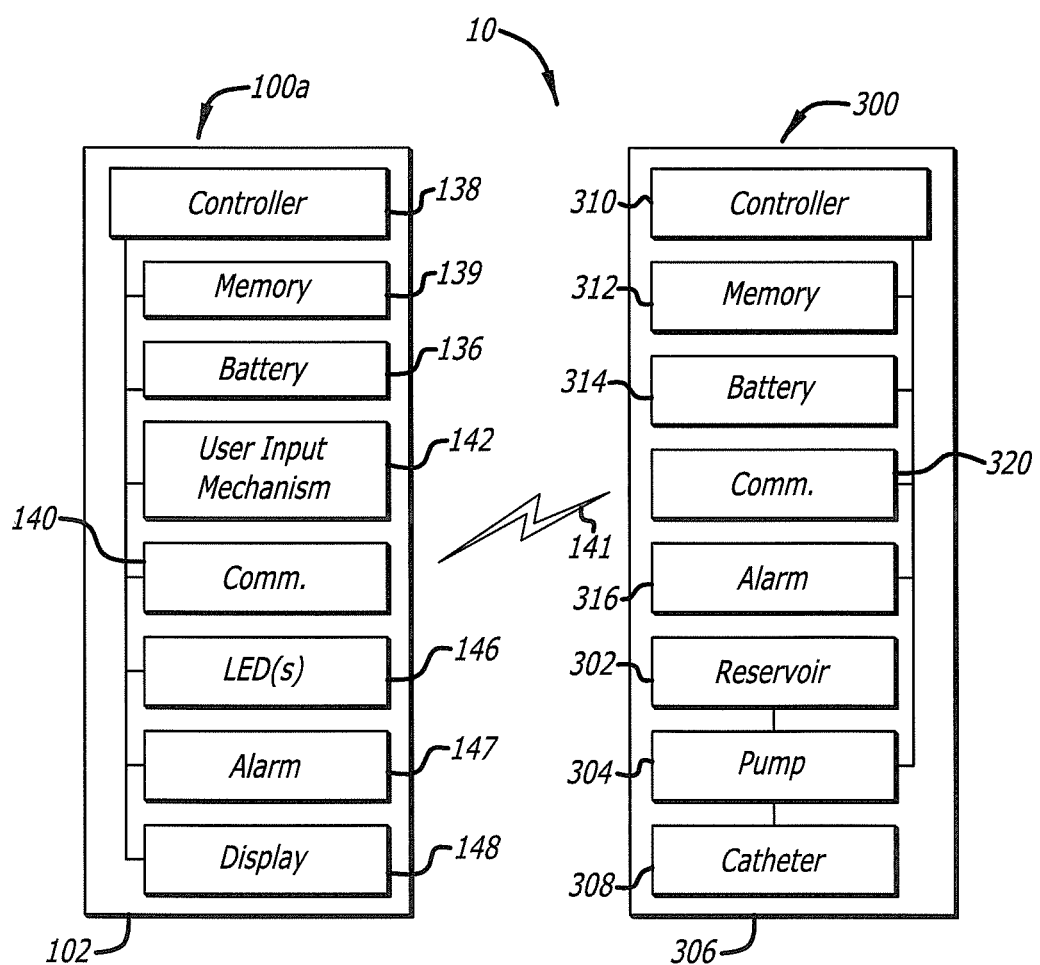
FIG. 3 is a block diagram of the programming device and implantable medical device of FIG. 2.

Referring again to FIG. 3, in this example embodiment, the controller 138 and memory 139 are contained within the housing 102 of the programmer 100a. The scope of the present invention also includes programmers or programming systems where the functionality of the controller 138, or a portion of this functionality, is "migrated" to a physical location that is external to the housing 102. Similarly, some or all of the memory 139 can be physically located external to the housing 102. Such external controller(s) and memory device(s) can be operatively interfaced with the programmer 100a with wireless or wired communication links.

In an example embodiment, a database of information relating to the implantable medical device 300 (e.g., an implantable drug pump) is stored in the memory 139. In an example embodiment, the information includes a list of clinician-approved drugs and dosage parameters such as rate, concentration, total daily dose, etc. associated with each of the drugs. In an example embodiment, a baseline database of information is initially uploaded into the memory 139. In an example embodiment, the controller 138 manages the function of uploading a database of information, as well as writing changes, additions or updates to the database of information. Under control of the controller 138 and in response to user inputs provided via the user input mechanism 142, the programmer 100a performs the various functions described herein, in particular, providing an interactive user interface, e.g., a graphical user interface (GUI), at the display 148.

Figure 6:
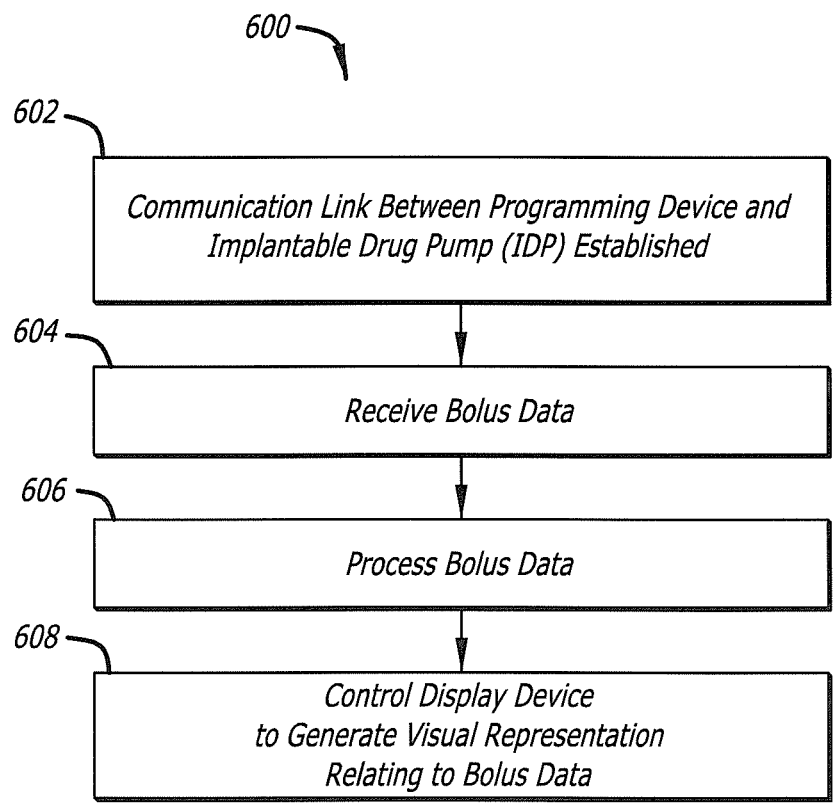
FIG. 6 is a flow chart in accordance with one embodiment of the present invention.

Referring to FIG. 6, in an example embodiment, a method 600 of generating a visual representation relating to bolus data for an implantable drug pump (IDP) is now described. At 602, a communication link between a programming device and an implantable drug pump (IDP) is established. For example, information uniquely identifying the IDP is received. In an example embodiment, the programming device (e.g., programmer 100a) is adapted to automatically recognize a pump that is within communications range. In another example embodiment, the programming device is not capable of recognizing a pump within communications range, rather the clinician is provided with a user option on the screen to recognize (uniquely identify) the pump. At 604, bolus data is received from the programming device. At 606, the bolus data is processed to control, at 608, the display device (e.g., display 148) to generate a visual representation relating to the bolus data.

Figure 7:
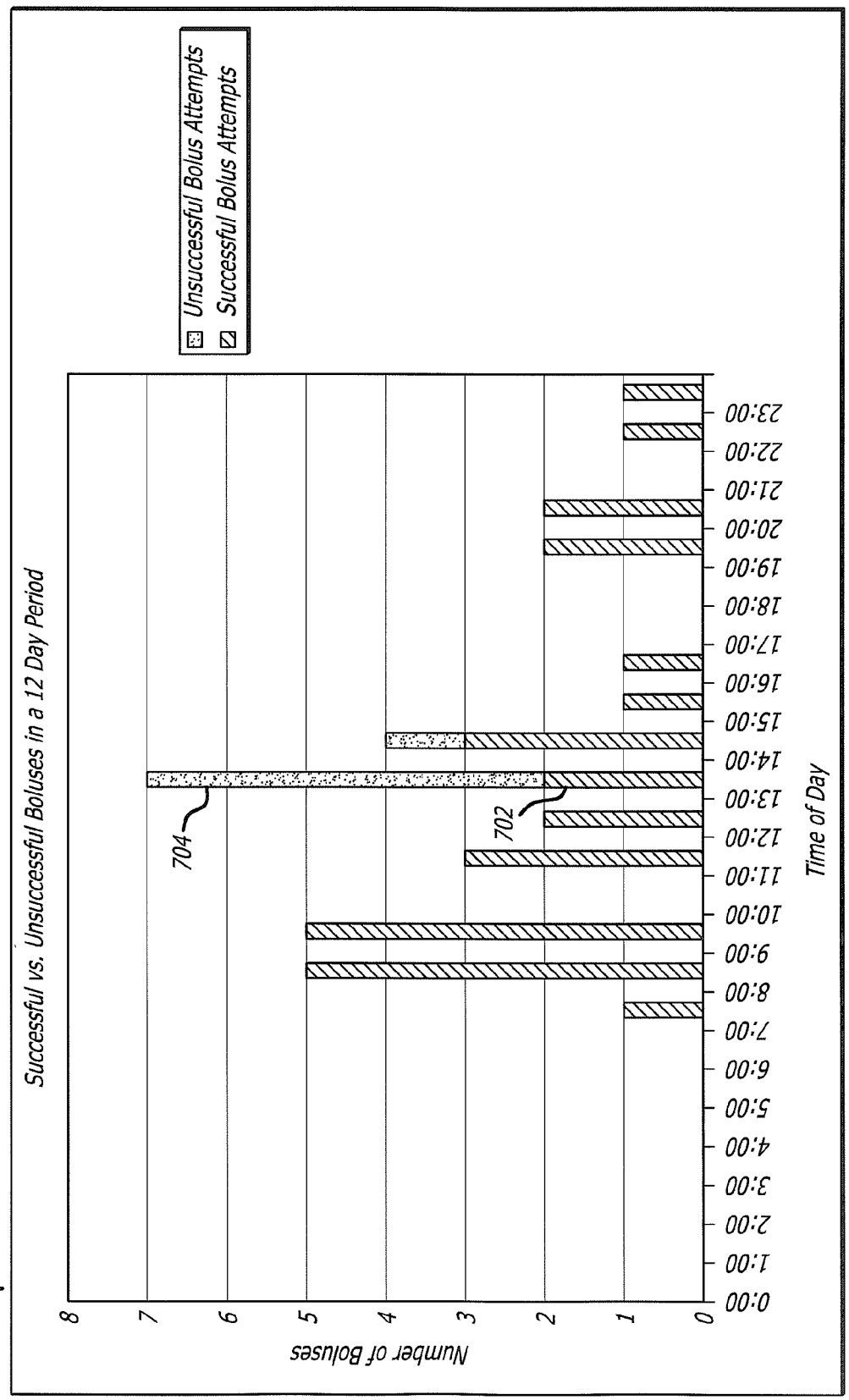
FIG. 7 shows a visual representation (of numbers of bolus attempts for multiple periodic time intervals) generated by a programming device according to an example embodiment of the present invention.

In an example embodiment, at 608, the programming device generates a visual representation 700 (FIG. 7) of numbers of bolus attempts for multiple periodic time intervals. In this example embodiment, the visual representation 700 includes a bar chart with visually distinct representations for successful and unsuccessful bolus attempts. In this example, bars 702 and 704 indicate two successful bolus attempts and four unsuccessful bolus attempts, respectively, at 13:00. It should be appreciated that the visual representations described herein are not limited to bar charts, and that the visual representations can include, for example: graphs, plots, diagrams, other types of charts, etc.

In an example embodiment, the visual representation 700 shows the numbers of bolus attempts between a beginning time (e.g., the time of the patient's last refill of the implantable drug pump 100a) and an end time (e.g., the time when the bolus data is received by the controller 138). Other beginning times and end times can also be used. In an example embodiment, one or more of the beginning time and the end time is selected by a user of the programming device. In an example embodiment, one or more of the beginning time and the end time is automatically or by default selected by the programming device (e.g., to track a programming device clock or the like).

In an example embodiment, the visual representation 700 shows the total number of successful boluses and the total number of unsuccessful boluses over multiple days (e.g., over a 12 day period). In another example embodiment, the visual representation 700 shows the average numbers of bolus attempts made within the multiple periodic time intervals. In these examples, the multiple periodic time intervals correspond to the hours of the day, i.e., there are 24 intervals. In example embodiments, the time intervals are contiguous and span the length of a day. In another embodiment, the time intervals are not necessarily contiguous, nor is it required that they span the length of a day. Also, the time intervals can vary in length. Generally, the time intervals partition a length of time into adjacent bins.

When the bolus data has been read by the programming device software, the data will be placed into bins. In this example embodiment, these bins are categorized by in hourly intervals or 24 bins. So if a bolus occurred at 9:15 a.m., the entry will be placed into the 9:00 a.m.-10:00 a.m. bin. This process will occur until all of the log entries from the start date to the end date have been placed into bins. Once the log entries have been sorted, the number of successful and unsuccessful bolus attempts is calculated for each bin.

In an example embodiment, the multiple periodic time intervals form a sequence of time intervals, and the controller 138 is adapted to temporally sort the bolus data and associate the bolus data with time intervals within the sequence depending upon when the bolus attempts were made. In an example embodiment, the controller 138 is adapted to calculate bolus attempts made within each of the time intervals, and the visual representation shows the calculated number of bolus attempts made within each of the time intervals. Thus, example programming devices described herein provide a visual representation of the frequency of bolus attempts made during different times (time intervals) of the day.

Example programming devices described herein provide visual representations of statistical data which allow a clinician to determine if the PCA regime is adequate and if not, modify the patient's daily regime and/or PCA regime, or provide alternative treatment. A clinician can configure a PCA profile for a given patient's pump. The typical elements of a PCA profile are: rate, duration, maximum allowable PCA boluses per day, and lockout period. The IDP logs all successful and unsuccessful PCA bolus attempts. Unsuccessful bolus attempts can be due to the fact that a bolus is currently ongoing (bolus lockout) or that the attempt has exceeded the number of boluses permitted (e.g., per day).

In an example embodiment, the controller 138 is adapted to generate an alert (e.g., by actuating LEDs 146 and/or the alarm 147) if a ratio of unsuccessful bolus attempts to successful bolus attempts made within one of the time intervals exceeds a threshold value. For example, if there are any bins where the unsuccessful bolus attempts to total number of bolus attempts ratio is above a clinician-defined threshold, the programming device automatically generates an alert. In an example embodiment, the controller 138 is adapted to generate a prompt inquiring whether a medication rate should be adjusted if a ratio of unsuccessful bolus attempts to successful bolus attempts made within one of the time intervals exceeds a threshold value. For example, the display 148 is controlled to suggest to the clinician "Ask the patient if everything is okay", or to adjust the therapeutic rate around the time of excessive unsuccessful bolus attempts. In an example embodiment, the controller 138 is adapted to facilitate adjustment of such threshold values by a user of the programming device (e.g., by prompting a user to provide an input to the programming device).

Figure 8:
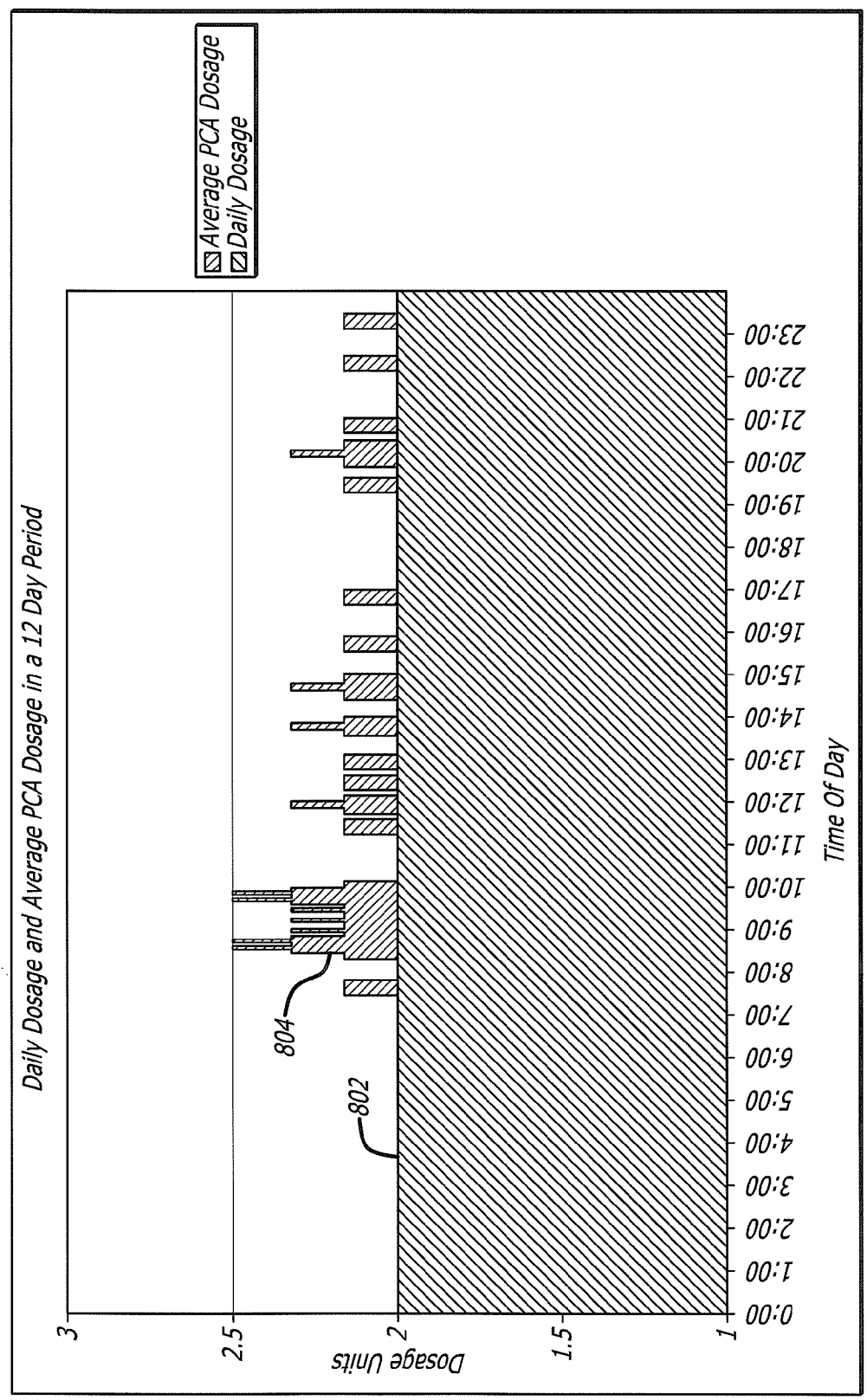
FIG. 8 shows a visual representation (of a daily drug delivery profile and an average patient-controlled analgesia (PCA) dose profile) generated by a programming device according to an example embodiment of the present invention.
Figure 10:
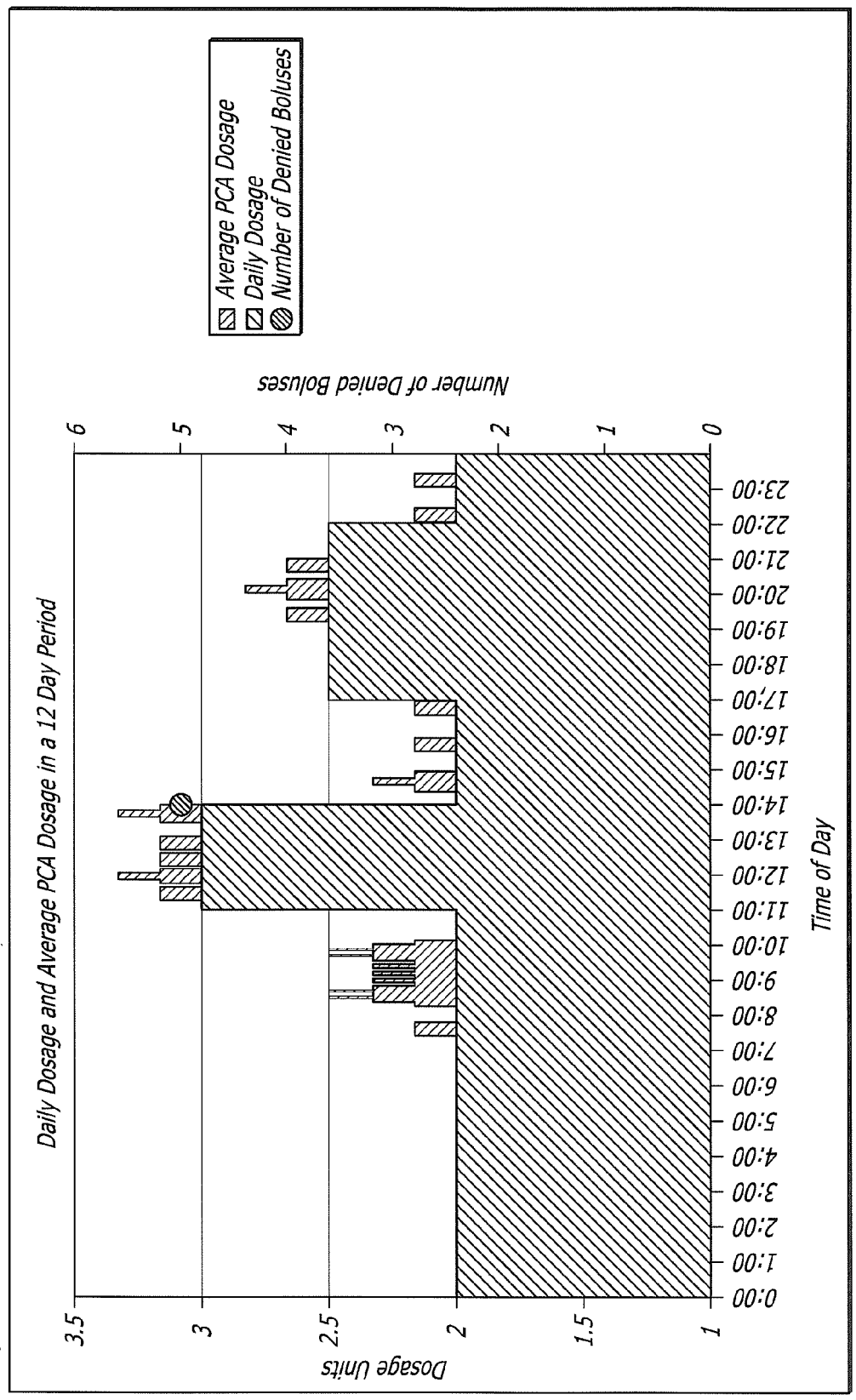

In another example embodiment, the programming device generates a visual representation 800 (FIG. 8) of a daily drug delivery profile 802 and an average patient-controlled analgesia (PCA) dose profile 804. In this example embodiment, the visual representation 800 provides a graphic of the daily delivery profile with the average PCA dosages overlaid on top. The daily drug delivery profile 802 and the average patient-controlled analgesia (PCA) dose profile 804 together show an average of how much drug is being delivered to the patient over the days during which the collected bolus data was analyzed. In this example embodiment, the controller 138 is adapted to generate the visual representation 800 such that the average PCA dose profile 804 overlays the daily drug delivery profile 802. The term "daily drug delivery profile" includes basal as well as temporary doses, i.e., doses that are not patient-controlled. In this example, the average daily drug delivery profile 802 is shown as being constant throughout the day; however, it should be appreciated that the daily drug delivery profile can specify different dosage levels for different times of the day (as shown in the visual representation 1000 depicted in FIG. 10).

Visual representations described herein can allow a clinician to determine if further treatment needs to take place, for example, to temporarily increase the therapeutic rate in places where the graph indicates that high PCA bolus average doses are being delivered. Thus, the clinician is presented with visual representations of data that has been recorded in the pump and can use that data to make delivery related changes, rather than relying solely on anecdotal information from the patient.

In an example embodiment, the controller 138 is adapted to generate the daily drug delivery profile 802 and the average PCA dose profile 804 over a time interval of use of the implantable drug pump (e.g., 12 days). In an example embodiment, the visual representation 800 is generated from bolus data received for bolus attempts made between a beginning time (e.g., the time of the patient's last refill of the implantable drug pump 100a) and an end time (e.g., the time when the bolus data is received by the controller 138). Other beginning times and end times can also be used. In an example embodiment, one or more of the beginning time and the end time is selected by a user of the programming device. In an example embodiment, one or more of the beginning time and the end time is automatically or by default selected by the programming device (e.g., to track a programming device clock or the like).

Figure 9:
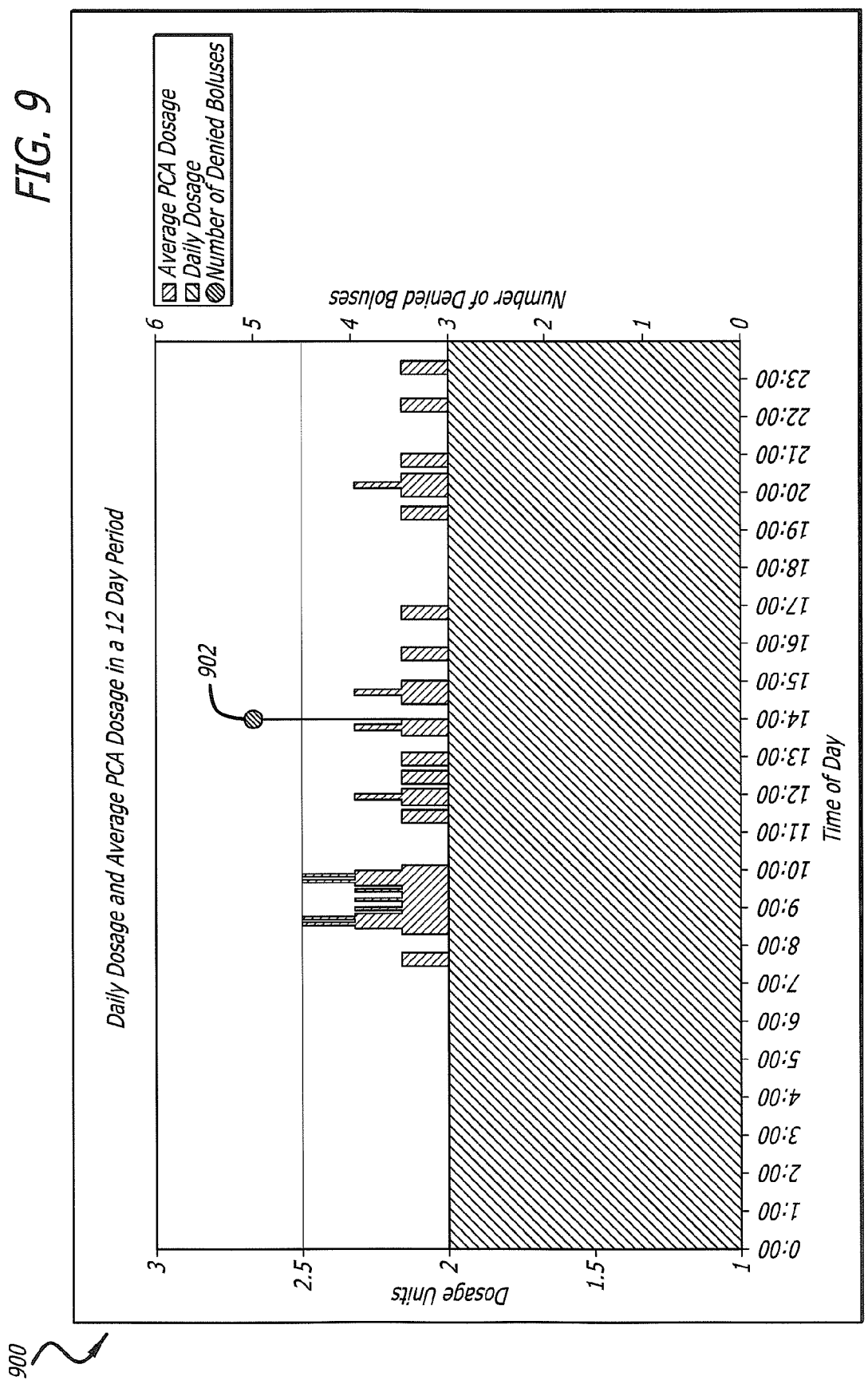
FIGS. 9 and 10 show visual representations (of a daily drug delivery profile, an average patient-controlled analgesia (PCA) dose profile, and denied boluses) generated by a programming device according to an example embodiment of the present invention.

Referring to FIG. 9, in another example embodiment, a visual representation 900 (similar to the visual representation 800) additionally includes an indicator 902 of when and the number of times PCA boluses were denied. In this example, five attempted boluses were denied at 13:00. Thus, in an example embodiment, the display device 148 is controlled to also generate a visual representation of denied boluses.

Although the invention disclosed herein has been described in terms of the preferred embodiments above, numerous modifications and/or additions to the above-described preferred embodiments would be readily apparent to one skilled in the art. The invention also includes any combination of the elements from the various species and embodiments disclosed in the specification that are not already described. It is intended that the scope of the present invention extend to all such modifications and/or additions and that the scope of the present invention is limited solely by the claims set forth below.

What is claimed is:

1. A programming device for an implantable drug pump, the programming device comprising:
    a display device;
    a communication device that facilitates a communication link between the programming device and an implantable drug pump; and
    a controller that receives bolus data stored on the implantable drug pump when the communications link has been established, processes the bolus data, and controls the display device to generate a visual representation of a daily drug delivery profile and an average patient-controlled analgesia (PCA) dose profile determined from the bolus data.

2. The programming device for an implantable drug pump of claim 1, wherein the daily drug delivery profile is an average daily drug delivery profile for multiple days.

3. The programming device for an implantable drug pump of claim 1, wherein the display device is controlled to also generate a visual representation of denied boluses.

4. The programming device for an implantable drug pump of claim 1, wherein the controller generates the daily drug delivery profile and the average PCA dose profile over a time interval of use of the implantable drug pump.

5. The programming device for an implantable drug pump of claim 1, wherein the controller generates the visual representation such that the average PCA dose profile overlays the daily drug delivery profile.

6. The programming device for an implantable drug pump of claim 1, wherein the bolus data is received for bolus attempts made between a beginning time and an end time.

7. The programming device for an implantable drug pump of claim 6, wherein one or more of the beginning time and the end time is selected by a user of the programming device.

8. The programming device for an implantable drug pump of claim 6, wherein the beginning time is the time of the patient's last refill of the implantable drug pump.

9. The programming device for an implantable drug pump of claim 6, wherein the end time is the time when the bolus data is received by the controller.

* * * * *